United States Patent
Alambeigi et al.

(10) Patent No.: US 10,688,656 B2
(45) Date of Patent: Jun. 23, 2020

(54) DEVICES WITH LOW MELTING POINT ALLOY FOR CONTROL OF DEVICE FLEXIBILITY

(71) Applicant: The Johns Hopkins University, Baltimore, MD (US)

(72) Inventors: Farshid Alambeigi, Ghazvin (IR); Reza Seifabadi, Baltimore, MD (US); Mehran Armand, Maple Lawn, MD (US)

(73) Assignee: The Johns Hopkins University, Baltimore, MD (US)

( * ) Notice: Subject to any disclaimer, the term of this patent is extended or adjusted under 35 U.S.C. 154(b) by 782 days.

(21) Appl. No.: 15/091,822

(22) Filed: Apr. 6, 2016

(65) Prior Publication Data
US 2016/0311108 A1    Oct. 27, 2016

Related U.S. Application Data

(60) Provisional application No. 62/153,175, filed on Apr. 27, 2015.

(51) Int. Cl.
*B25J 9/06* (2006.01)
*B25J 18/06* (2006.01)
(Continued)

(52) U.S. Cl.
CPC .............. *B25J 9/06* (2013.01); *A61B 1/0051* (2013.01); *A61B 1/0055* (2013.01); *A61B 1/00078* (2013.01); *A61B 1/128* (2013.01); *A61M 25/005* (2013.01); *A61M 25/0054* (2013.01); *B25J 9/065* (2013.01); *B25J 9/1095* (2013.01);
(Continued)

(58) Field of Classification Search
CPC . B25J 18/06; B25J 9/0015; B25J 9/065; B25J 9/1095; B25J 19/0075; A61M 25/0054; A61B 1/00078; A61B 1/0051; A61B 1/0055; A61B 1/128;
(Continued)

(56) References Cited

U.S. PATENT DOCUMENTS 4,517,632 A    5/1985  Roos
4,697,978 A *  10/1987  Tada .................... B25J 17/0241
                                                    414/729
(Continued)

FOREIGN PATENT DOCUMENTS

EP          2 067 580         6/2009
WO     WO-2012043178 A1 *  4/2012  ......... A61B 1/00154

OTHER PUBLICATIONS

Cheng, Nadia et al., "Design and Analysis of a Soft Mobile Robot Composed of Multiple Thermally Activated Joints Driven by a Single Actuator," Conference Paper for IEEE International Conference on Robotics and Automation, IEEE Xplore DOI: 10.1109/ROBOT.2010.5509247, Jun. 2010, pp. 1-6.
(Continued)

*Primary Examiner* — Joseph Brown
(74) *Attorney, Agent, or Firm* — Noah J. Hayward

(57) ABSTRACT

A continuum device/manipulator includes a first flexible tube, a low melting point (LMP) alloy disposed within the first flexible tube, and a temperature adjustment element that applies heat or cooling to change a phase of the LMP alloy. Changing the phase of the LMP alloy controls a flexibility of the first flexible tube.

18 Claims, 16 Drawing Sheets

(51) Int. Cl.
*B25J 9/10* (2006.01)
*B25J 15/12* (2006.01)
*A61M 25/00* (2006.01)
*A61B 1/005* (2006.01)
*A61B 1/12* (2006.01)
*A61B 1/00* (2006.01)
*A61B 17/00* (2006.01)

(52) U.S. Cl.
CPC ............... *B25J 15/12* (2013.01); *B25J 18/06* (2013.01); *A61B 2017/00411* (2013.01); *A61B 2017/00955* (2013.01)

(58) Field of Classification Search
CPC ........... A61B 2017/00411; A61B 2017/00955; A61B 25/0054
USPC .................. 74/490.04, 49; 901/21; 604/531
See application file for complete search history.

(56) References Cited

U.S. PATENT DOCUMENTS

| | | | | |
|---|---|---|---|---|
| 4,790,624 | A | * | 12/1988 | Van Hoye ............ A61B 1/0058 385/118 |
| 7,766,896 | B2 | | 8/2010 | Kornkven Volk et al. |
| 8,882,165 | B2 | | 11/2014 | Lipson et al. |
| 2006/0211979 | A1 | * | 9/2006 | Smith ................ A61B 18/1492 604/11 |
| 2008/0009831 | A1 | * | 1/2008 | Griffin ................ A61M 25/005 604/531 |
| 2008/0169729 | A1 | * | 7/2008 | Asai ........................ A61F 2/50 310/363 |
| 2009/0124857 | A1 | * | 5/2009 | Viola ................... A61B 1/0055 600/141 |
| 2010/0010441 | A1 | * | 1/2010 | Belson .............. A61M 25/0054 604/104 |
| 2011/0082538 | A1 | * | 4/2011 | Dahlgren ......... A61B 17/00234 623/2.11 |
| 2011/0227455 | A1 | * | 9/2011 | Nagamitsu ............. B25J 9/1095 310/333 |
| 2014/0109560 | A1 | | 4/2014 | Ilievski et al. |
| 2014/0378945 | A1 | | 12/2014 | Beri |
| 2015/0352728 | A1 | * | 12/2015 | Wang ...................... B25J 18/06 74/490.04 |
| 2017/0292502 | A1 | * | 10/2017 | Tonazzini .............. B22D 19/00 |

OTHER PUBLICATIONS

Kim, Yong-Jae et al., "Design of a Tubular Snake-like Manipulator with Stiffening Capability by Layer Jamming," 2012 IEEE/RSJ International Conference on Intelligent Robots and Systems, Oct. 7-12, 2012, Vilamoura, Algarve, Portugal, pp. 4251-4256.

Shan, Wanliang et al., "Soft-matter composites with electrically tunable elastic rigidity," Smart Mater. Struct. 22 (2013) 085005, pp. 1-8.

* cited by examiner

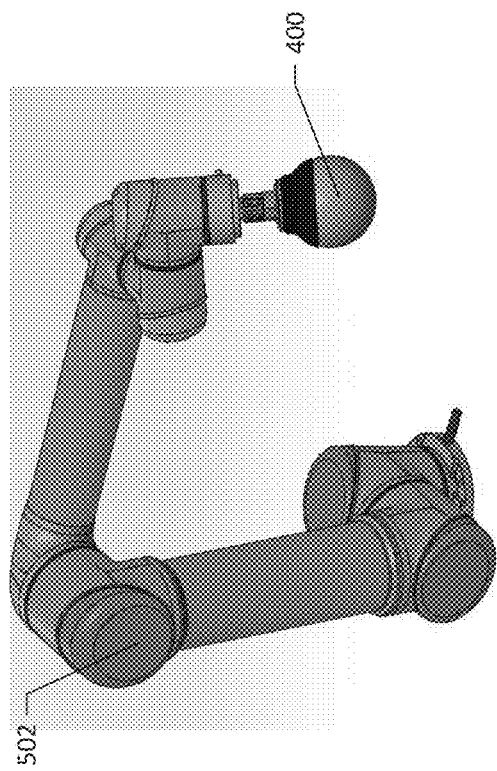
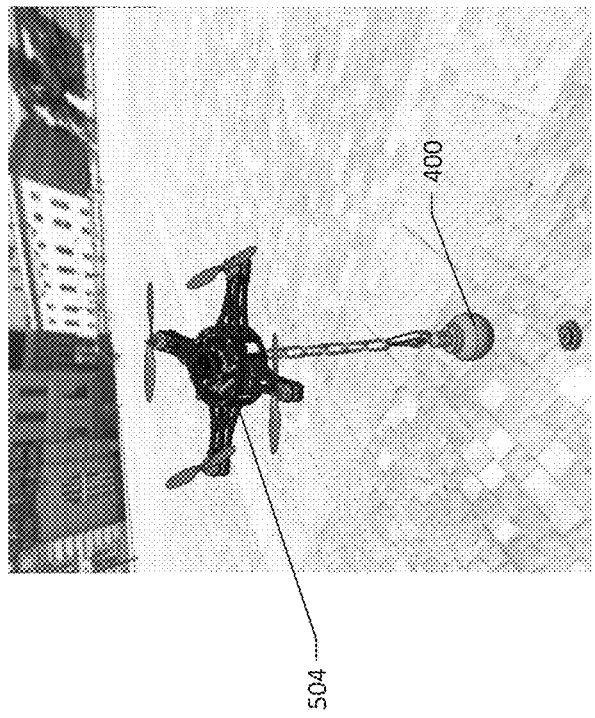
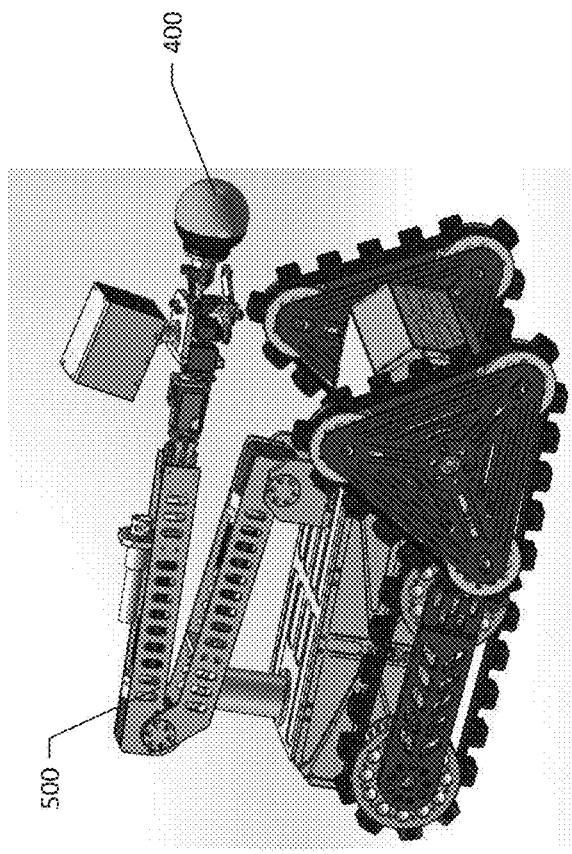
FIG. 16A
FIG. 16B
FIG. 16C

DEVICES WITH LOW MELTING POINT ALLOY FOR CONTROL OF DEVICE FLEXIBILITY

CROSS REFERENCE TO RELATED APPLICATIONS

This application claims the benefit of U.S. Provisional Application No. 62/153,175 filed on Apr. 27, 2015, the entire contents of which are hereby incorporated herein by reference.

STATEMENT OF GOVERNMENTAL INTEREST

This invention was made with Government support under contract number 1R01EB016703-01A1 awarded by the National Institutes of Health (NIH). The Government has certain rights in the invention.

TECHNICAL FIELD

Example embodiments generally relate to continuum devices and, in particular, relate to devices with a Low Melting Point (LMP) alloy for control of device flexibility.

BACKGROUND

Snake-like devices/manipulators have a wide variety of uses in various industrial, medical, and general fields for positioning and/or holding objects. However, these devices/manipulators and arms are generally constructed to meet one of two objectives, flexibility or strength. An example of a continuum device may be a continuum manipulator used in the medical field. Continuum manipulators may generally be constructed of a flexible polymer tube, which may be snaked to the desired location bending around obstructions. However, the typical continuum manipulator may have limited strength to maintain a particular position when pushed against an object, such as during drilling, cutting, probing, or the like. Reaction force or other external forces from these operations may cause the typical continuum manipulator to be displaced away from the desired position. This may be particularly problematic in applications requiring high accuracy, such as medical procedures.

In contrast, devices that are constructed to have high strength may be limited in flexibility. For example, articulated arms generally include a plurality of rigid segments with joints. The rigid segments may prevent the snaking utilized by more continuum devices.

Typical gripping or grasping manipulators may be complex and may not morph around an object of interest while preserving the strength of the grip. For instance, a pinch gripper may be simple and have a relatively high strength, but have very limited dexterity and flexibility. More complex grippers may be significantly more physically and computationally complex.

A recent solution utilizes a granular material in a continuum or elastic membrane. The device may be activated, e.g. become stiff or rigid, by applying a vacuum to the membrane causing a jamming effect of the granular material. The device may be when not activated and become rigid when activated. However, the device may be limited by vacuum pressure, require a bulky vacuum system, and require vacuum to be applied continuously when activated.

A gripper utilizing the granular material and a vacuum may have a very high dexterity, but as discussed above, the strength is limited by the vacuum, which must be continuously supplied. Further, the gripper utilizing the granular material and vacuum may also require the bulky vacuum system, which must be again continuously applied when activated.

BRIEF SUMMARY OF SOME EXAMPLES

Accordingly, some example embodiments may enable a continuum device/manipulator to be provided including a first flexible tube, a LMP alloy disposed within the first flexible tube, and a temperature adjustment element configured to apply heat or cooling to change a phase of the LMP alloy. Changing the phase of the LMP alloy controls flexibility of the first flexible tube.

In another embodiment, a grasper is provided including a flexible membrane, a LMP alloy is disposed within the flexible membrane, and a temperature adjustment element configured to apply heat or cooling to change the phase of the LMP alloy. Changing the phase of the LMP alloy controls the flexibility of the flexible membrane.

BRIEF DESCRIPTION OF THE SEVERAL VIEWS OF THE DRAWING(S)

Having thus described the continuum device/manipulator in general terms, reference will now be made to the accompanying drawings, which are not necessarily drawn to scale, and wherein:

FIGS. 16A-16C illustrate example positioning systems for a grasper according to an example embodiment.

DETAILED DESCRIPTION

Figure 2A:
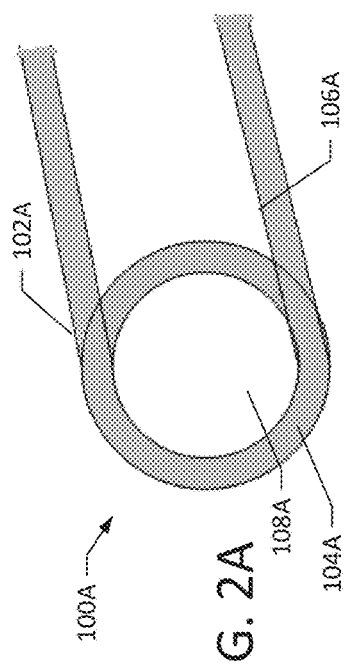
FIGS. 2A-2C illustrate example configurations of a device with LMP alloy according to an example embodiment.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. As used herein, operable coupling should be understood to relate to direct or indirect connection that, in either case, enables functional interconnection of components that are operably coupled to each other.

In an example embodiment, a continuum device/manipulator is provided including a LMP alloy which may selectively change phases to control the flexibility of the continuum device/manipulator. A temperature adjustment element, such as a resistive heater or coolant provided by a coolant pump may cause the change in phase of the LMP alloy by changing the temperature. The ability to control the flexibility of the continuum device/manipulator may allow for the device/manipulator to be positioned while flexible. Then changing the phase of the LMP alloy may cause the continuum device/manipulator to be rigid at a desired location. The rigidity at the desired location may significantly increase a payload capacity of the continuum device/manipulator.

In some example embodiments, the temperature adjustment element may include a plurality of segments that may individually apply heat or cooling to the LMP alloy. A controller may be utilized to control the application of heat and cooling allowing for on demand binary stiffness of each segment of the continuum device/manipulator. Utilizing steering cables in conjunction with the on demand binary stiffness of the segments may allow for precise steering of the continuum device/manipulator around objects, which may not have been possible using typical device/manipulators.

In some example embodiments, a grasper is provided that utilizes the LMP alloy. The LMP alloy may be disposed within an elastic membrane. The grasper may engage an object while the LMP alloy is in a liquid phase, which may conform or morph to contours of the object. The LMP alloy may then change to a solid phase, which may cause a rigid engagement with the object. Since the grasper conforms to the contours of the object before becoming rigid, the grasper may have a significantly higher grip strength than typical grippers. Thus the grasper may be capable of holding heavier objects.

In embodiments of the continuum device/manipulator and/or the grasper, a relatively small power supply may be used to supply power to the temperature adjustment element, which may also be relatively simple in design and implementation. Additionally, once the LMP alloy is in solid phase, power is not required to maintain the LMP alloy in the solid phase. As such, the continuum device/manipulator may maintain a desired shape or grip indefinitely.

Example LMP Alloys

In an example embodiment, a LMP alloy may be utilized to change the flexibility of a continuum device/manipulator or a conforming grasper. The LMP material may be an alloy, such as Field's metal, Wood's metal, or the like; thermoplastic polymers; rheological gel; or the like. Non-toxic alloys, such as Field's metal may be preferable in medical fields or other fields in which exposure to the LMP alloy is possible or likely. Field's metal is described in the examples herein to illustrate the principals of the LMP alloy. However, these examples are in no way limiting. One of ordinary skill in the art would immediately appreciate that other LMP alloys, such as those described above may be used depending on the application.

The LMP alloy may have a low melting point, such as 62° C. for Field's metal. Additionally, the LMP alloy may be a eutectic alloy. For example, Field's metal is a eutectic alloy of bismuth, indium, and tin. Specifically, Field's metal includes the following percentages by weight 32.5% Bi, 51% In, and 16.6% Sn. Field's metal may have a high stiffness in the solid phase and capability to bear high external loads with a low melting point.

Example Continuum Device/Manipulator

Figure 1:
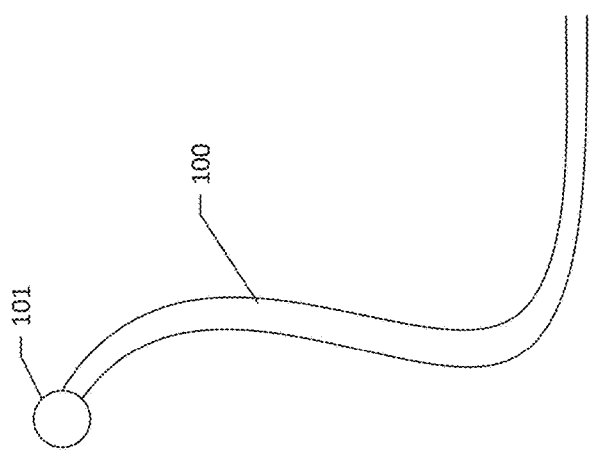
FIG. 1 illustrates an example continuum device/manipulator according to an example embodiment.

FIG. 1 illustrates an example continuum device/manipulator 100 according to an example embodiment. The continuum device/manipulator 100 may include an LMP alloy to change the flexibility of the continuum device/manipulator, as discussed below. The continuum device/manipulator 100 may be configured to change flexibility or stiffness on demand allowing for the continuum device/manipulator 100 to be snaked or steered to a desired position, while the continuum device/manipulator is in a "soft state," e.g. the LMP alloy is in the liquid phase. Once the continuum device/manipulator reaches the desired position, the LMP alloy may change to a solid phase transitioning the continuum device/manipulator to a "rigid state." The eutectic properties of the LMP alloy may allow for a rapid transition between the liquid phase and solid phase.

In an example embodiment, the continuum device/manipulator 100 may include a tool 101 at the distal end of the continuum device/manipulator 100. For example, the tool may include a gripper, a cutter, such as cutting blade, drill bit, or milling blade, a manipulator, or the like as described below in reference to FIGS. 15 and 16, or the like. The continuum device/manipulator 100 may be scalable for applications ranging from small intravascular device/manipulators and catheters to large industrial drilling operations.

Figure 2B:
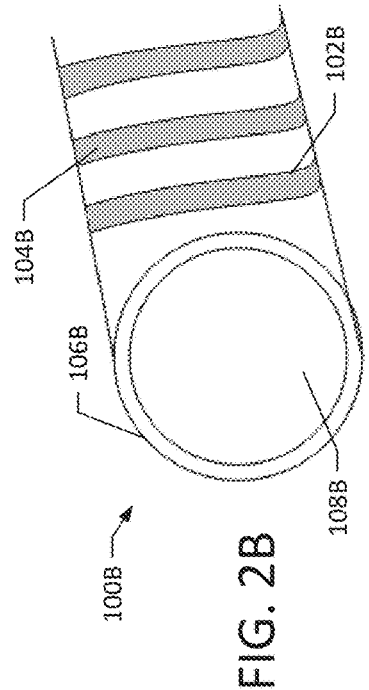
Figure 2C:
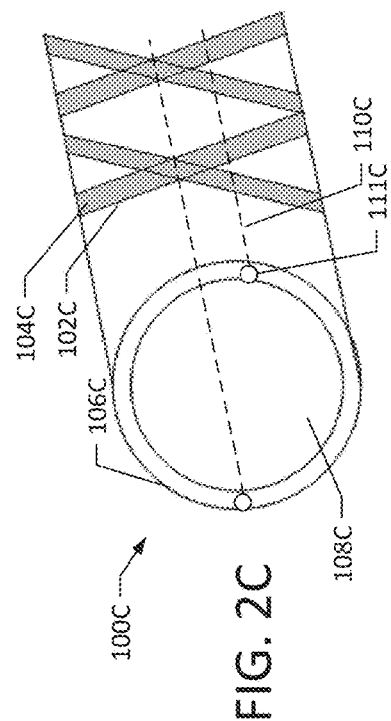

FIGS. 2A-2C illustrate example configurations of a LMP according to an example embodiment. FIG. 2A depicts a lateral cross-section of a continuum device/manipulator 100A, including an outer tube 102A, an inner tube 106A, and a LMP alloy 104A. The outer tube 102A and inner tube 106A may be a continuum polymer or silicon tube. In this example embodiment, the LMP alloy 104A is disposed in a space between the outer tube 102A and the inner tube 106A. The inner tube 106A may have an open center lumen 108A. The lumen 108A may be configured to pass devices, such as catheters, drills, cameras, or the like; fluids, such as lubricant, coolant, medicines, or the like; control electronics, such as wires or cabling; or the like.

In the example continuum device/manipulator 100B depicted in FIG. 2B, the outer tube 102B may be filled with the LMP alloy 104B. The outer tube 102B may be wrapped around the inner tube 106B in a helical spiral. Alternatively, the outer tube 102B may be a helical spiral disposed within the inner tube 106B.

In the example continuum device/manipulator 100C depicted in FIG. 2C, the outer tube 102C may be disposed in a lattice pattern around the exterior or interior of inner tube 106C. The lattice structure of outer tube 102C may have a common channel at crossing points of the lattice or include separate channels. Although three examples of the outer tube 102C and LMP alloy 104 configurations are depicted, one of ordinary skill in the art would immediately appreciate other configurations may be employed depending on the application, such as interconnected or interlocking figure eights.

The example continuum device/manipulator 100 depicted in FIG. 2C also includes steering wires 110C or cables. The steering wires 110C may be used to cause the continuum device/manipulator to bend in the soft state. The steering wires 110C may be anchored to anchor points 111C on a collar disposed at the outer surface of the continuum device/manipulator 100C and/or the distal end of the continuum device/manipulator 100C. Pulling on the steering wires 110C may cause an eccentric point load at the anchored points 111C causing the bending of the continuum device/manipulator 100C. Furthermore, shape memory alloys, such as heat activated Nitinol wires, may be used for actuation of the continuum device/manipulator.

Figure 3:
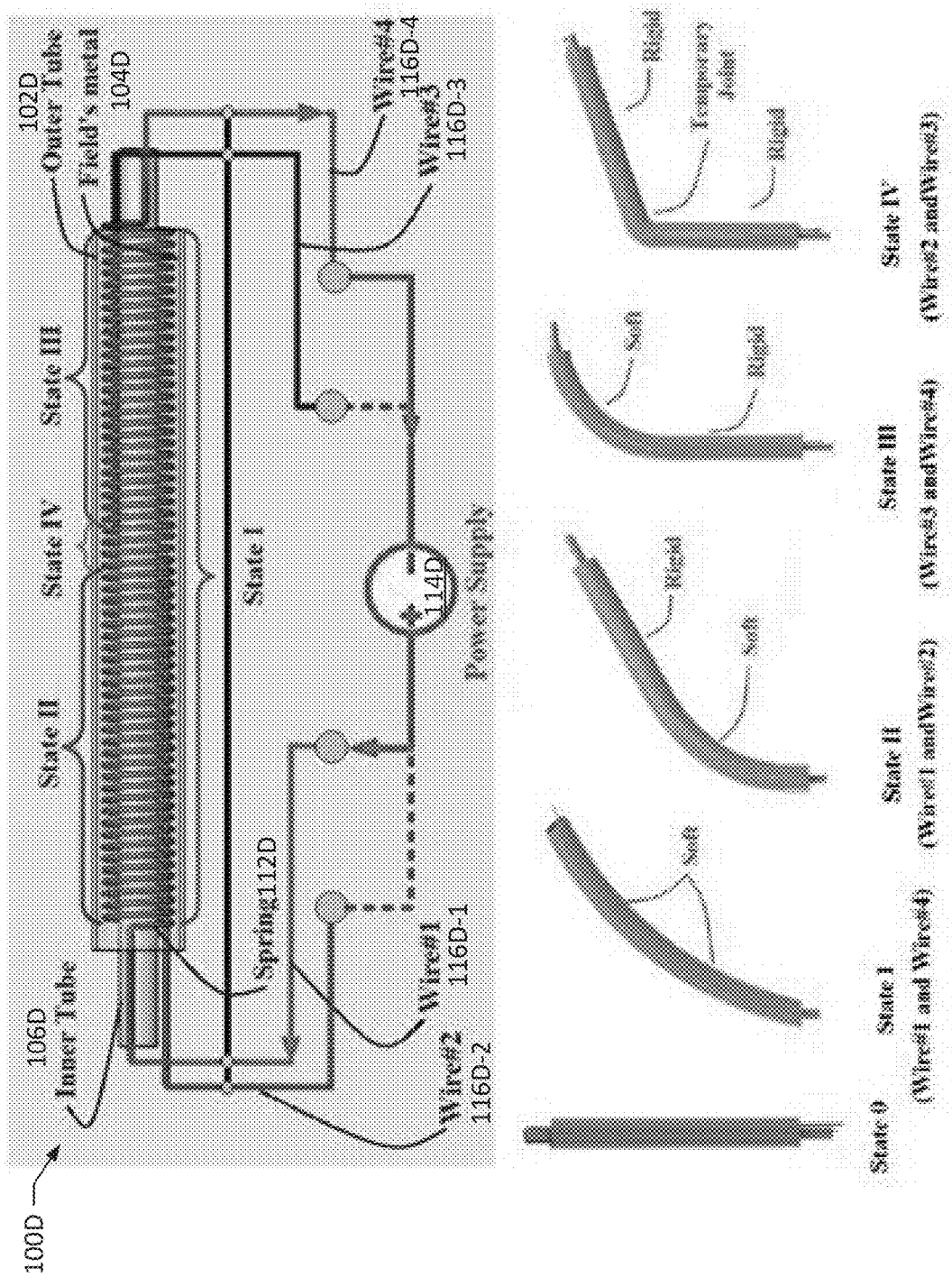
FIG. 3 illustrates an example schematic of a continuum device/manipulator according to an example embodiment.

FIG. 3 illustrates an example schematic of a continuum device/manipulator 100D according to an example embodiment. The continuum device/manipulator 100D may include an outer tube 102D, an inner tube 106D, and a PCA 104D disposed between the outer tube 102D and inner tube 106D. The continuum device/manipulator 100 may also include a spring 112D, a power supply 114D, and electrical wires 116. The spring 112 may be helical in shape and disposed between the inner tube 106 and outer tube 102. The spring 112 may provide a support structure to prevent kinking of the continuum device/manipulator 100. The spring 112 may also provide a mode of force to return the continuum device/manipulator to a normal or straight position without exerting energy on the steering wires, such as steering wires 110C, or servo motors. Additionally, the spring 112D may be configured as a portion of a temperature adjustment element. The temperature adjustment element, as discussed below may include a heating element and/or a cooling element to apply heat or cooling to the LMP alloy 104D to cause a change in phase of the LMP alloy 104D.

The spring 112 may be configured to be a resistive continuum heater. The power supply 114D may supply electrical current to the spring 112D. The resistance of the spring 112D may cause the spring 112D to increase in temperature and cause the LMP alloy 104D to increase in temperature to a low melting point, for example 62° C. in the case of Field's metal. In an instance in which the heating of the spring 112D causes the LMP alloy 104D to reach or exceed the melting point of the LMP alloy 104D, the LMP alloy 104D may change phase from a solid to a liquid. The continuum device/manipulator 100D may be flexible, e.g. soft, in an instance in which the LMP alloy 104D is in the liquid phase, and be inflexible, e.g. rigid, in an instance in which the LMP alloy 104 is in the solid phase.

In some example embodiments, the continuum device/manipulator 100D may include a plurality of segments which may be individually controlled, e.g. change phase of the LMP alloy 104D. In an example embodiment, the segments may be defined by electrical connections at various points of the spring 112D. A controller, as discussed below in reference to FIG. 18, may be utilized to selectively apply current to the various segments of the spring 112D.

For example, in state 0, no portion of the spring 112D is energized and the entire continuum device/manipulator 100D is rigid. In state I, current is supplied through wire (1) 116D-1 and wire (4) 116D-4, in this condition, the entire length of the spring 112D is energized. Energizing the entire spring 112D may cause the LMP alloy 104D along the entire length of the continuum device/manipulator 100D to be change to a liquid phase, causing the continuum device/manipulator 100D to be in the soft state. In stage II, current is applied to a lower segment of the spring 112D defined by wire (1) 116D-1 and wire (2) 116D-2. The lower portion of the continuum device/manipulator 100D, associated with the lower segment, transitions to the soft state. An upper segment, which is not energized, remains in the rigid state. In state III, current is applied to the segment of the spring 112D defined by the wire (3) 116D-3 and wire (4) 116D-4. The upper portion of the continuum device/manipulator 100D, associated with the upper segment, transitions to the soft state. The lower segment, which is not energized, remains in the rigid state. In state IV, a current is applied to a mid segment defined by wire (2) 116D-2 and wire (3) 116D-3, which is between the upper segment and the lower segment. The mid segment transitions to the soft state, creating a temporary joint in the continuum device/manipulator 100D. The upper segment and lower segment, which are not energized, remain in the rigid state.

In States I, II, III, and IV, portions of the continuum device/manipulator 100D in the soft state may be steered by snaking the continuum device/manipulator 100D or pulling the steering wires 110D. Once the continuum device/manipulator 100D, or portion of the continuum device/manipulator 100D, is in the desired position, the temperature adjustment element may cause the LMP alloy 104D to change phase to the solid phase. In an example embodiment, the temperature adjustment element may terminate current flow to the continuum device/manipulator 100D or segment of the spring 112D. The LMP alloy 104D may cool utilizing ambient heat transfer or may be actively cooled by supplying, via a coolant pump, a coolant to the LMP alloy 104D. The coolant may be water, lubricant, low temperature gas, or the like. In some example embodiments, the coolant may be supplied through a lumen, similar to lumen 108A.

In some embodiments, the adjustable temperature element may additionally or alternatively include joule heating, resistive wires, Kapton heaters, and/or a hot fluid, which may be passed through the lumen. Furthermore, other heating methods such as induction heating or ultrasound waves can be used from outside of the device.

In an example embodiment, the stiffness of the LMP alloy 104D may depend on the modulus of elasticity and the moment of inertia of the continuum device/manipulator 100D. In the liquid phase, stiffness and modulus of the elasticity may be dictated by the stiffness of the spring 112D. In the solid phase of the LMP alloy 104D, however, the spring 112D may be surrounded with the LMP alloy 104D as a composite beam behaving as two parallel springs. In other words, the stiffness of the solid phase LMP alloy 104D may be added to that of the spring 112D. To maintain the shape of the continuum device/manipulator 100D after bending, the added stiffness of the LMP alloy 104D may overcome elastic energy stored in the bent spring 112D. The added stiffness of the LMP alloy 104D may also be a function of the modulus of elasticity and moment of inertia of the LMP alloy 104D and therefore may be a function of geometry of the composite beam geometry. The spring 112D may help to withstand more external load because a stiffness of the spring 112D may be added to the stiffness of the LMP alloy 104D and reinforces the composite beam.

In an example embodiment, the spring 112D, or other temperature adjustment element, may be surrounded by the LMP alloy 104D, as discussed above, and it may be assumed that the generated heat entirely transfers to the LMP alloy 104D. It may also be assumed that for a spring 112D with a constant pitch, the resistive heating will be uniform along the length of the spring 112D:

$$Ri^2 t = mc\Delta\theta + mL_f$$

$$m = \rho V$$

where m is the mass, V is the volume, $\rho=9700$ kg/m3 is the density, $c=172$ J/kgK is the specific heat capacity, $L_f=39980$ J/kg is the latent heat of LMP alloy 104, Field's metal in the present example, $\Delta\theta$ is the difference of the room temperature and melting point of Field's metal (62° C.), R is the spring resistance, i is the current, and t is the duration of applying current. Using this equation, a response time of the system may be determined based on the generated heat and the amount of Field's metal used.

In some example embodiments, compactness, response time, and energy consumption of the system are three important design parameters in designing the spring 112D. From a mechanical aspect, stiffness (k) of the spring 112D may be calculated as follows:

$$k = Gd^4/8nD^3$$

where G is the modulus of the rigidity, d is the wire diameter, D is the mean coil diameter, and n is the number of active coils of the spring.

From a thermodynamics aspect, electrical resistance of the spring 112 may be defined as:

$$R = \rho L/A$$

where $\rho$ is the electrical resistivity, R is the electrical resistance, L is the length, and A is the cross-sectional area of wire.

The above equations may illustrate that increasing the wire diameter increases the spring stiffness, but decreases the electrical resistance, thereby increasing the time required to change the phase of the LMP alloy 104D.

In an example embodiment, a single-segment continuum device/manipulator 100 may be provided. The spring 112D may be a Polytetrafluoroethylene (PTFE) coated stainless steel #304 wire with diameter of 0.635 mm (0.025 inch). The PTFE coating thickness may be between 0.004 mm and 0.01 mm and configured to withstand 195° C. The spring 112D may have a 9.8 mm outer diameter, a 1 mm pitch, and a 50 mm length. Measured resistance of the spring 112D may be 2.56 ohms. The outer tube 102D and inner tube 106D may be continuum silicon rubber tubes (Shore A35). The inner tube 106D may have an outer diameter of 9.52 mm and a wall thickness of 1.59 mm. The outer tube 102D may have a wall thickness of 3 mm and an inner diameter of 10 mm. A LMP alloy 104D, of Field's metal (such as manufactured by RotoMetals, Inc), may be disposed between the inner tube 106D and outer tube 106D. The power supply 114D may pass the electric current through the spring 112D generating 30 W with constant voltage of 8.5 V and corresponding current of 3.32 A. The average response time for melting the LMP alloy 104D, e.g. the Field's metal, from 45° C. to 62° C. may be about 3.5 seconds.

In another example embodiment, a two-segment continuum device/manipulator may be provided. The spring 112 may be a PTFE stainless steel wire with a length of 72 in. The spring 112 may have an outer diameter of 9.8 mm, pitch of 1 mm, and length of 115 mm. The inner tube 106 and outer tube 102 may be a super soft silicon rubber. The diameter of the inner tube 106 may be 8 mm. Resistance of the spring 112 may be 5.25 ohms. Two steering wires, similar to steering wires 110C may be anchored to anchor point, similar to anchor points 111C, of opposing external collars attached to the outer surface of the outer tube 102D for steering the continuum device/manipulator 100D. The power supply and wires may supply electricity to the spring 112D in a manner similar to FIG. 3 including the configuration of the wires 116D-1, 2, 3, 4 and segments of the spring 112D. Thereby allowing for the shape and flexibility of each segment to be controlled separately. In this example, the temperature adjustment element includes a coolant pump, configured to pass cold water, e.g. 4° C. with a 900 ml/min flow rate, through the lumen. The continuum device/manipulator 10D may also include a controller, as discussed below in reference to FIG. 18, configured to apply current to the wires 116-1,2,3,4 and respective segments of the spring 112D to achieve States), I, II, III, and IV.

In an example embodiment, the melting time of the LMP alloy 104D may be decreased for a respective power increase. For example, melting time may decrease from 36.7 seconds to 8.2 seconds for heating from 25° C. to 62° C. and from 19.9 seconds to 3.1 seconds for heating from 45° C. to 62° C., based on a power increase from 26.4 W to 74 W. Similarly, higher power may decrease a phase changing time of the LMP alloy 104. For example, the phase change time may decrease from 15 seconds at 26.4 W (3 A) to about 2.5 seconds at 74 W (5 A). Furthermore, at 61° C. the continuum device/manipulator 100D may be soft enough to be shaped by pulling the steering wires, while the LMP alloy 104D has not completely transformed to the liquid phase. Therefore, heating the LMP alloy 104D, e.g. Field's metal up to 61° C. rather than 62° C. may reduce the phase change time (to about 5.7 seconds for heating from 25° C. and 2 seconds for heating from 45° C.) while having sufficient flexibility to change the shape of the continuum device/manipulator 100D.

Similar to heating, as the power increases, the corresponding cooling time may decreases since the surface temperature may remain lower during high power heating. Cooling water may significantly reduce the cooling time or natural cooling, e.g. convection, to ambient environment. For example, the cooling time with water from 62° C. to 45° C. may be 58 seconds and 177 second using natural convection.

In an example embodiment, the continuum device/manipulator 100D including 20 g of LMP alloy 104D, e.g. Field's metal, and having a length of 12 cm, a diameter of 13 mm, and a slenderness ratio of 9 may be capable of withstanding a 1000 gram force without deformation in the rigid state, e.g. 50 times the weight of the LMP alloy 104D.

Figure 4:
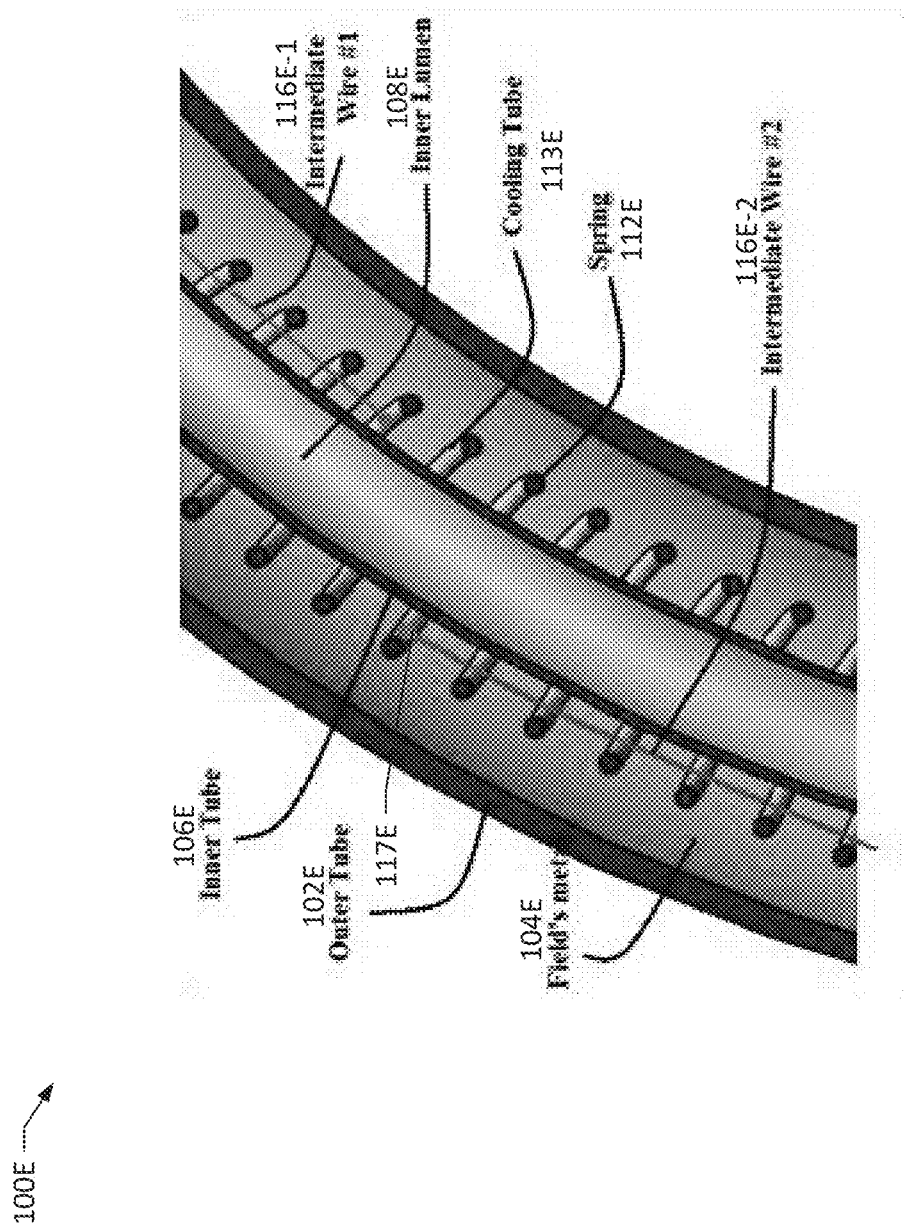
FIG. 4 illustrates an example cross-section of a continuum device/manipulator according to an example embodiment.

FIG. 4 illustrates example cross-section of a continuum device/manipulator 100E according to an example embodiment. The continuum device/manipulator 100 may include an outer tube 102E, an inner tube 106E, and a LMP alloy 104E. In this example, the LMP alloy 104E is Field's metal disposed between the inner tube 106E and the outer tube 102E. The continuum device/manipulator 100E may also include a spring 112E and wires 116E-1,2 disposed within the LMP alloy 104E. The wires 116E-1,2 may be connected to the spring 112E at electrical connections 117E. In some example embodiments, the continuum device/manipulator 100E may be cooled by coolant flow through the lumen 108E. Additionally or alternatively, the coolant may flow through a cooling tube 113E. The cooling tube 113E may be disposed within the LMP alloy 104E. Embedding the cooling tube 113E in the LMP alloy 104E may allow for more efficient cooling of the LMP alloy 104E, which may result in faster phase transition between the liquid phase and the solid phase. In an example embodiment, the cooling tube 113E may, additionally or alternatively, pass hot fluid to heat the LMP alloy 104E.

Figure 5:
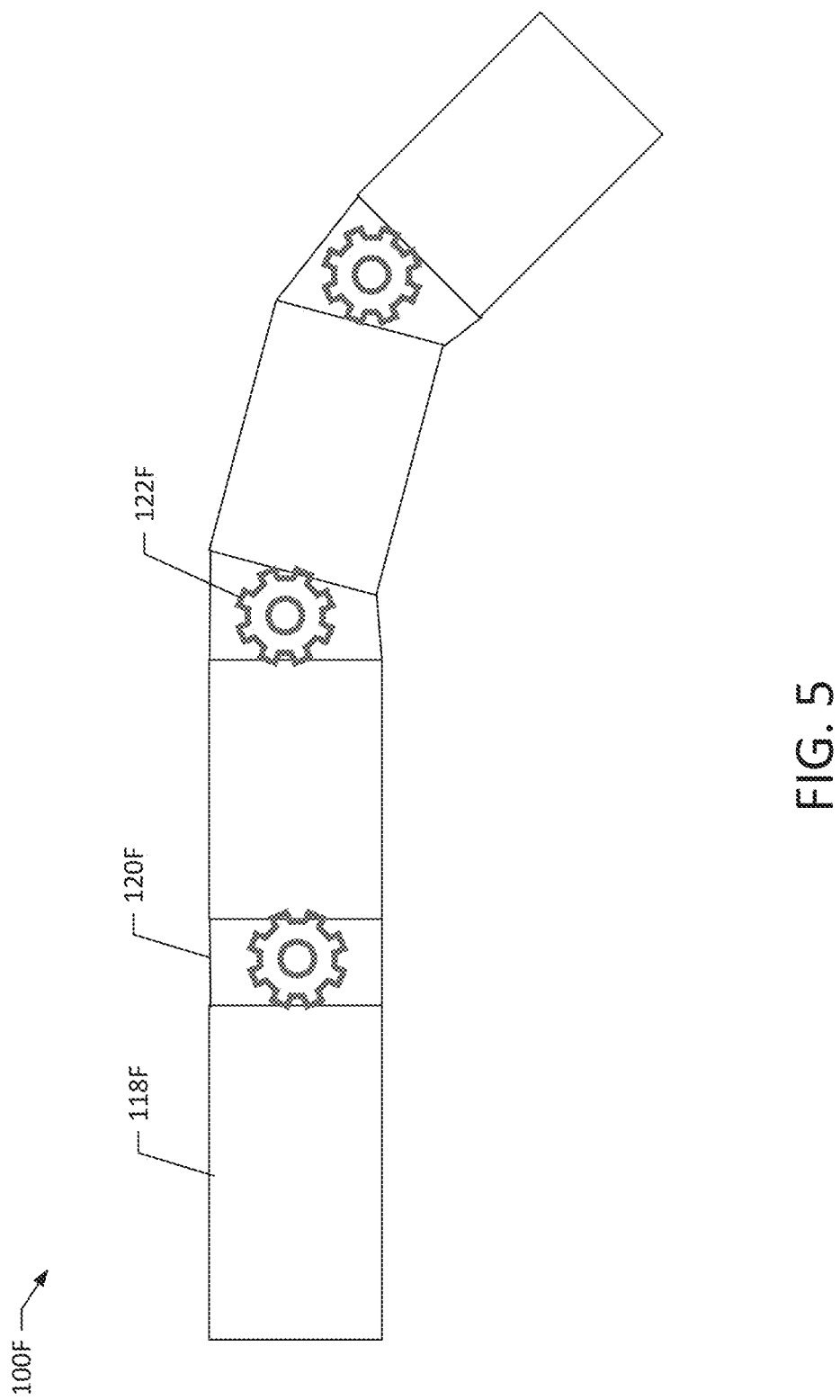
FIG. 5 illustrates an example continuum device/manipulator with non-continuum segments according to an example embodiment.

FIG. 5 illustrates an example continuum device/manipulator 100F with non-continuum segments 118F according to an example embodiment. The continuum device/manipulator 100F may include one or more non-continuum segments 118F. For example, an outer tube, similar to outer tube 102A, LMP alloy, similar to LMP alloy 104, and temperature adjustment element may be contained within an in continuum material, such as metal, e.g. stainless steel, or rigid plastic, e.g. Polyvinyl chloride (PVC) or medical grade plastics. The continuum device/manipulator 100F may have joints 120F at which a gap is present between the non-continuum segments 118F. The joints 120F may be selectively transitioned between the soft state and rigid state to position or steer the continuum device/manipulator 100.

In some example embodiments, the positioning or steering the continuum device/manipulator 100 may be executed utilizing steering wires, similar to steering wires 110C as discussed above in reference to FIGS. 2C and 3. Additionally or alternatively, the joints 120F may include actuation motors 120F or steering motors, e.g. servo motors. In an example embodiment, the actuation motors 122F may be disposed within a membrane to prevent the LMP alloy from entering the actuation motors 122F. The actuation motors 122F may position the joints 120F when the joints 120F are in the soft state. The joints 120F may then be transitioned to the rigid state. Once in the rigid state, the joints 118F may retain the position without joint locks or motor force. In other words, power may not be necessary to maintain the position of the rigid joints 118F.

Figure 6:
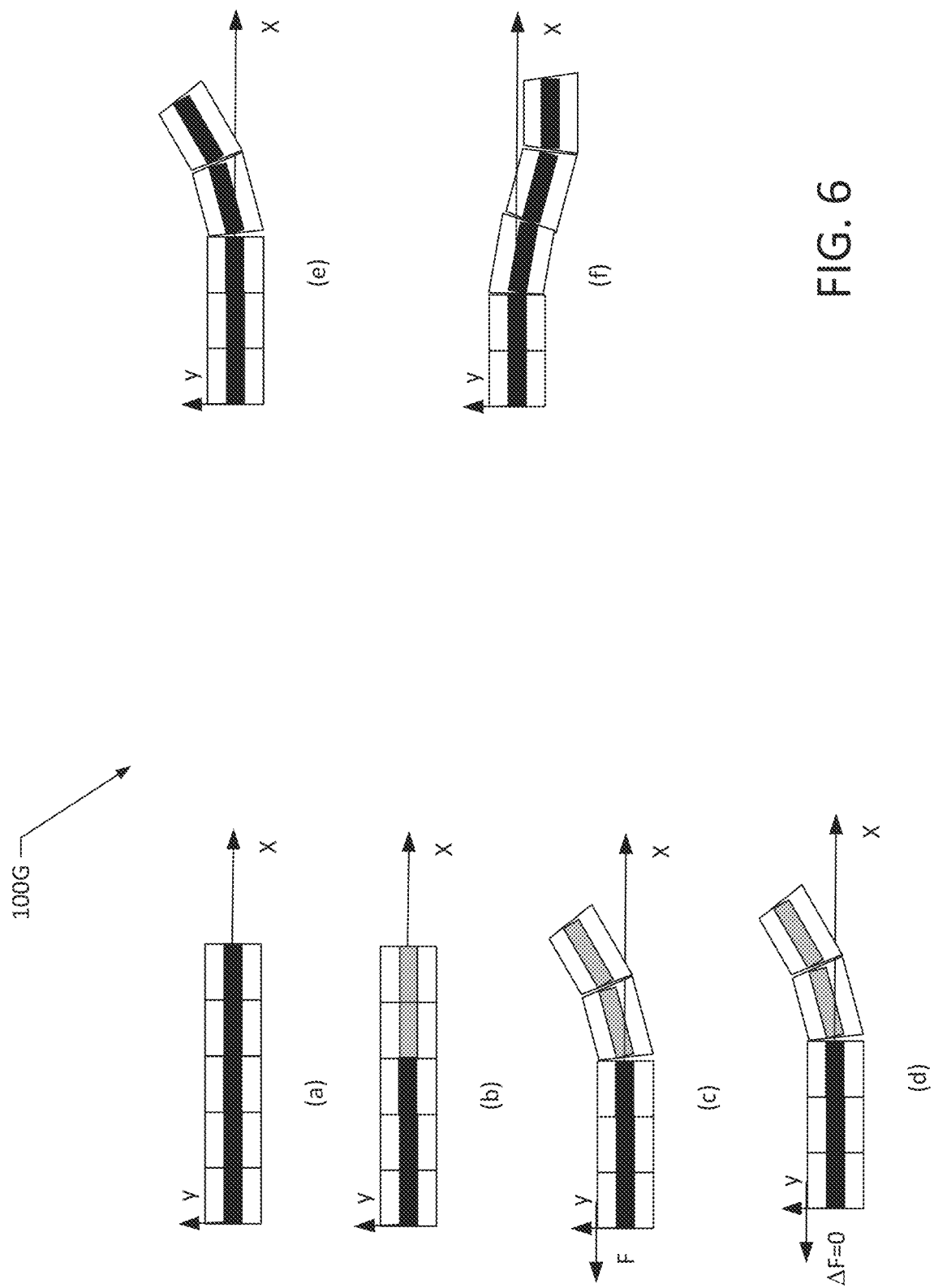
FIG. 6 illustrates an example of a continuum device/manipulator with on demand binary stiffness according to an example embodiment.

FIG. 6 illustrates an example of a continuum device/manipulator 100G with on demand binary stiffness according to an example embodiment. The depicted continuum device/manipulator 100G includes five segments, which may be transitioned between the soft state and rigid state on demand, such as by a controller, as discussed below in reference to FIG. 18. The continuum device/manipulator 100G changes shape from time a through time f. At time a, the continuum device/manipulator 100G is straight and each of the five segments is in the rigid state, which is indicated by the dark center section. At time b, the first two segments, indicated by the extension of the longitudinal axis x, have been transitioned to the soft state. The soft state of the segments is indicated by the light center sections. At time c, a force F is applied, such as by the steering wire 110C. The force F pulls the top of the continuum device/manipulator 100G rearward applying a point load to the distal end of the continuum device/manipulator 100G. The point load causes the continuum device/manipulator 100G to bend upward in the y axis. At time d, the force F is held and the temperature adjustment element stops applying heat to a LMP alloy, such as LMP alloy 104C. At time e, the first two segments have transitioned to the rigid state, due to the cooling of the LMP alloy. Time f illustrates a configuration of the continuum device/manipulator 100G in which the last three segments have been positioned in the opposite direction, e.g. downward, by a process similar to the process described in reference to times a-e.

Figure 7:
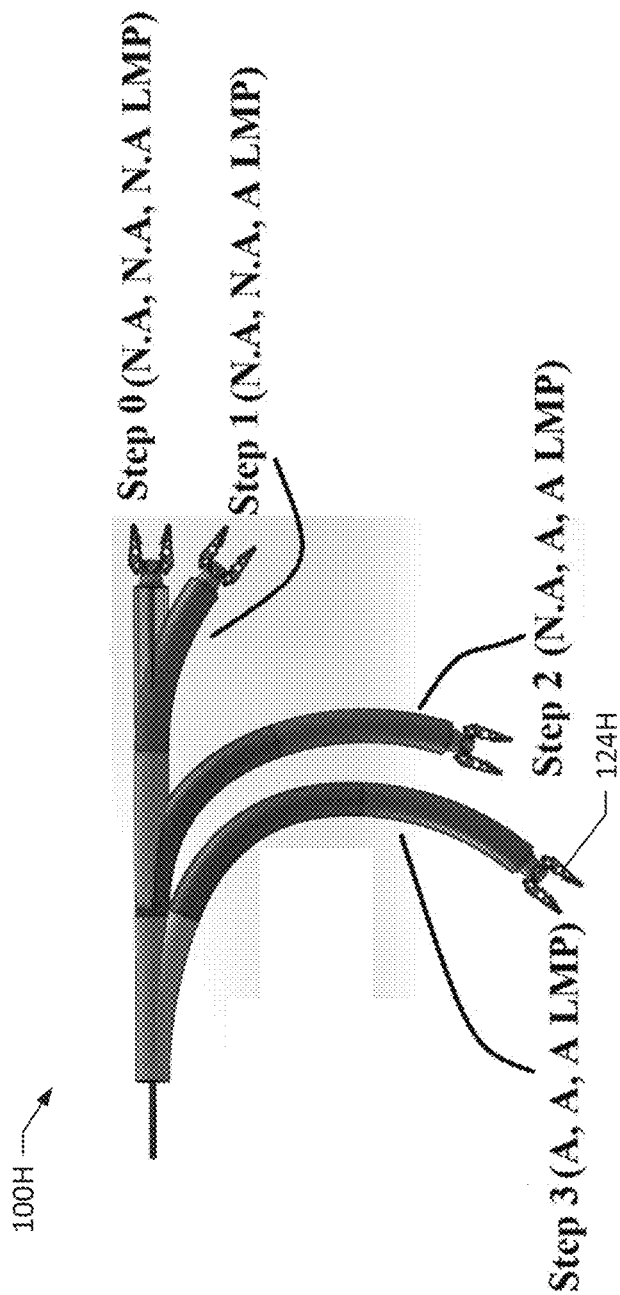
FIG. 7 illustrates a segmented continuum device/manipulator according to an example embodiment.

FIG. 7 illustrates a segmented continuum device/manipulator 100H according to an example embodiment. The continuum device/manipulator 100H may include three segments and a gripper 124H. The gripper 124H may be configured to pass through the lumen 108 or be mounted to the distal end of the continuum device/manipulator 100. The continuum device/manipulator 100H may include four possible flexation steps, e.g. steps 0, 1, 2, and 3. In step 0, each of the segments may be in the rigid state, e.g. not activated (N.A.), in which the LMP material 104, e.g. LMP, is in the solid phase. Each of the segments of the continuum device/manipulator 100 may be resistant to movement of flexation in Step 0.

In Step 1, the first segment, proximate to the gripper 124H, may be in the soft state, e.g. activated (A), in which the LMP material is in the liquid state. The first segment may be continuum or steerable to a desired position. The second and third segments may be rigid and resist flexation. In Step 2, the first two segments of the continuum device/manipulator 100H may be in the soft state, and the third segment may be in the rigid state. The first two segments may be continuum or steerable and the third segment may resist flexation. At Step 3, each of the three segments may be in the soft state and may be continuum or steerable. The more segments which are in the soft state, the more the continuum device/manipulator 100H may be able to flex or turn.

Figure 8:
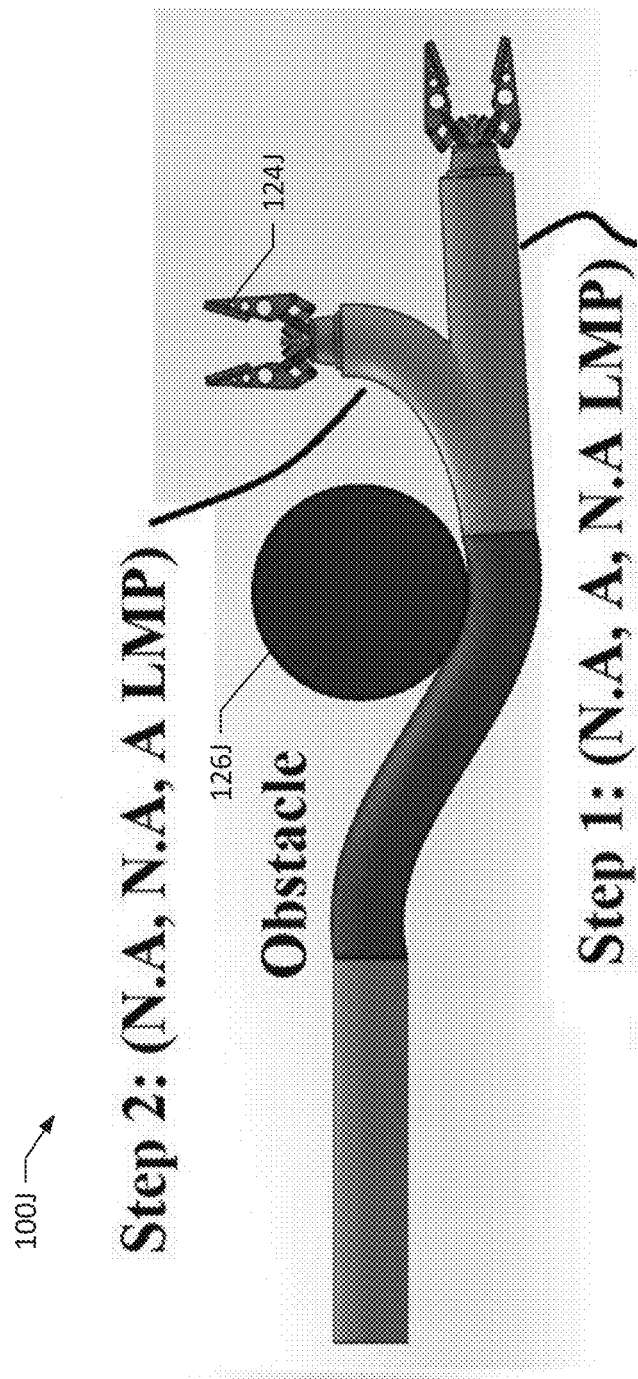
FIG. 8 illustrates navigation of a segmented continuum device/manipulator around an obstacle according to an example embodiment.

FIG. 8 illustrates navigation of a segmented continuum device/manipulator 100J around an obstacle 126J according to an example embodiment. In an example embodiment, the continuum device/manipulator 100J may have segments transition between the soft and rigid state on demand to assist in the navigation around the obstacle 126J. For example, in Step 1, the continuum device/manipulator 100J may have the second segment in soft state and the first and third segment in a rigid state, allowing the continuum device/manipulator 100 to snake around the obstacle 126J. In step 2, the continuum device/manipulator 100J may have the first segment in the soft state and the second and third segments in the rigid state. This configuration, in which only the first segment is continuum, allows for the first segment to be steered behind the obstacle 126J, which may not be possible using conventional devices. Additionally or alternatively, depending on the configuration of wires, such as wires 116D-1,2,3,4, the lengths of the segments may be lengthened or shortened to achieve different curvatures, by selecting specific ones of the wires.

In a comparison of a typical continuum endoscope and a continuum device/manipulator endoscope according to an example embodiment. The typical continuum endoscope may need a significant rigidity to be snaked through the media, in this example the colon and lower intestine. Additionally, steering the typical continuum endoscope bends the length of the endoscope. The rigidity of the typical continuum endoscope may cause deformation of the media. In the present example, deformation of the colon and lower intestine may occur. In contrast, the continuum device/manipulator endoscope may be less rigid and more precisely steered through a media, therefore not causing deformation of the media. Once the continuum device/manipulator endoscope has been steered to the desired position, the continuum device/manipulator endoscope may be transitioned to the rigid state. In the rigid state, tools may be passed through the lumen 108 to perform manipulations with accuracy and safety, even while enduring significant external forces, such as 3 kg.

Similarly, in the case of working within an incision, the typical continuum endoscope may be limited in the angle of approach, for example grabbing tissue with an endoscopic grasper. The continuum device/manipulator endoscope may be steerable to provide a more desirable or direct angle of approach.

Figure 9:
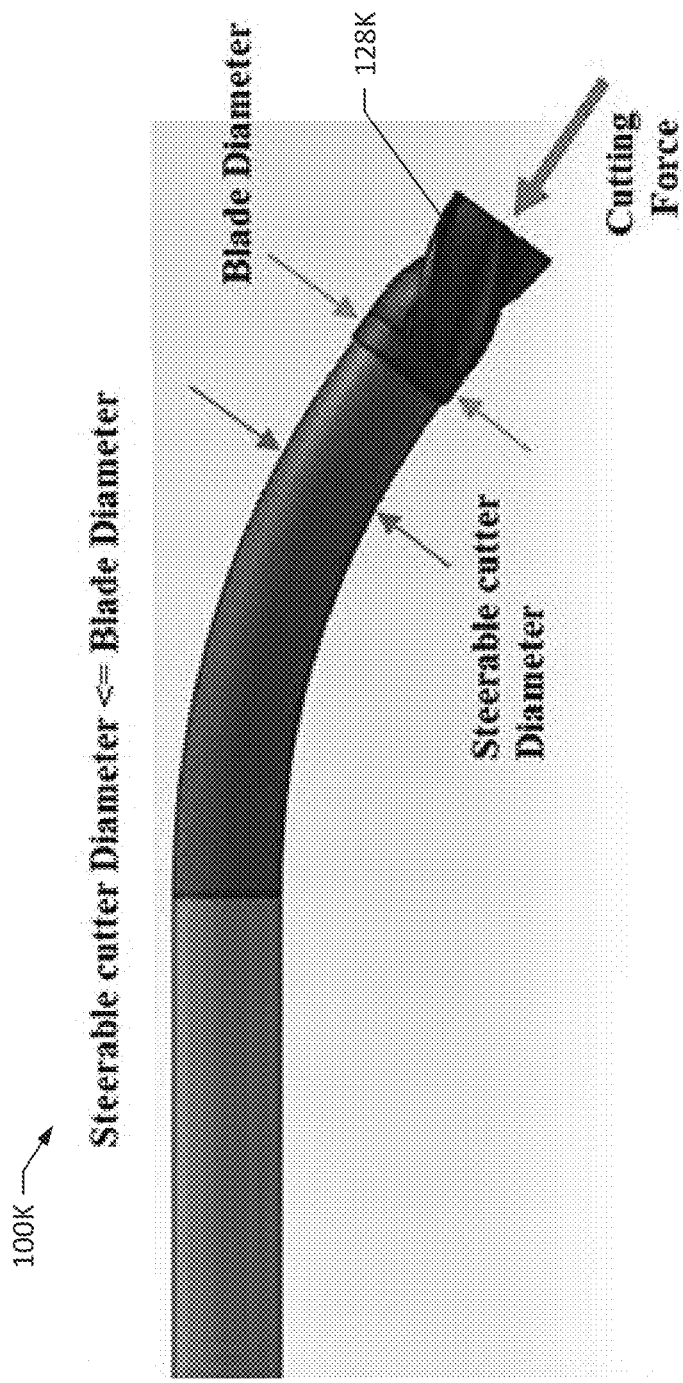
FIG. 9 illustrates a continuum device/manipulator employed as a steerable cutter according to an example embodiment.
Figure 10:
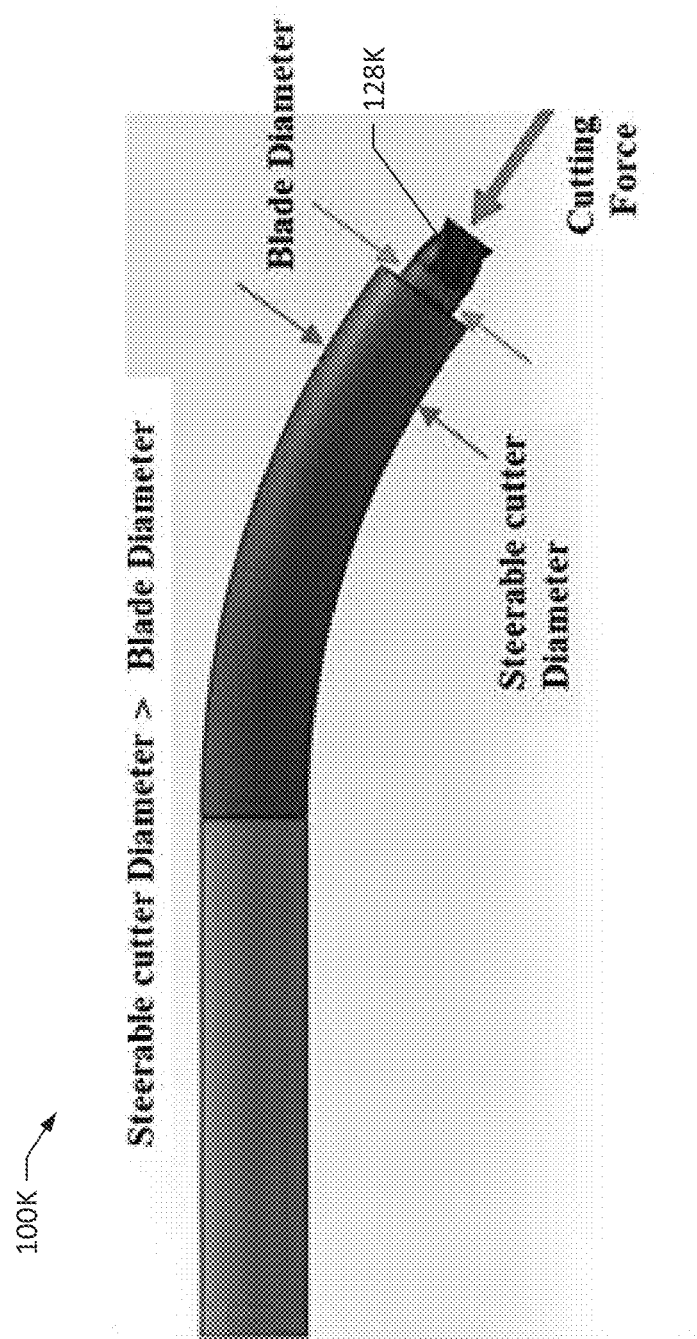
FIG. 10 illustrates a continuum device/manipulator employed as a steerable cutter according to an example embodiment.

FIGS. 9 and 10 illustrate a continuum device/manipulator 100K employed as a steerable cutter according to an example embodiment. In an example embodiment, the continuum device/manipulator 100K may include a cutter 128K, such as a cutting blade, rotating head, drill, edge, milling blade, or file. The cutter 128K may be mounted to the distal end of the continuum device/manipulator 100K, as depicted in FIG. 9, or may be passed through a lumen, similar to lumen 108A, as depicted in FIG. 10. In an example embodiment in which the cutter 128K is mounted to the distal end of the continuum device/manipulator 100K, the diameter of the cutter 128K may be at least as wide as the outer diameter of the inner tube, and may be equal to or greater than the outer diameter of the continuum device/manipulator 100K. In an instance in which the cutter 128K is passed through the lumen, the cutter 128K may have a diameter less than the inner diameter of the lumen.

The continuum device/manipulator 100K may provide a high accuracy placement of the cutter 128K due to the on demand phase transition and steering, as discussed above in FIG. 8. Further, as discussed in reference to FIG. 3, once the continuum device/manipulator 100K is in the desired position, the continuum device/manipulator 100K may be transitioned to the rigid state and have a high resistance to flexation. The resistance to flexation may allow for a greater cutting force to be applied without the continuum device/manipulator 100K buckling or moving from the desired position. Further, the continuum device/manipulator 100K may be resistant to vibration, which may be advantageous during milling.

Figure 11:
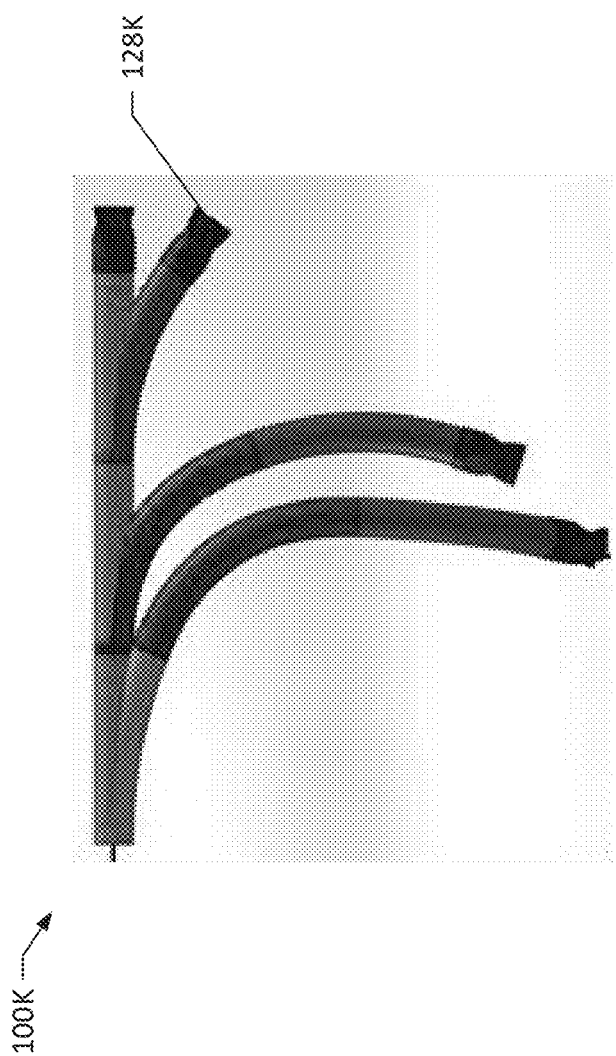
FIG. 11 illustrates a segmented continuum device/manipulator employed as a steerable cutter according to an example embodiment.

FIG. 11 illustrates the segmented continuum device/manipulator 100K employed as a steerable cutter. The continuum device/manipulator 100K depicted in FIG. 12 may be substantially similar to the continuum device/manipulator 100H depicted in FIG. 7. However, the continuum device/manipulator 100K of FIG. 12 is configured with a cutter 128K, instead of the gripper 124H.

Figure 12:
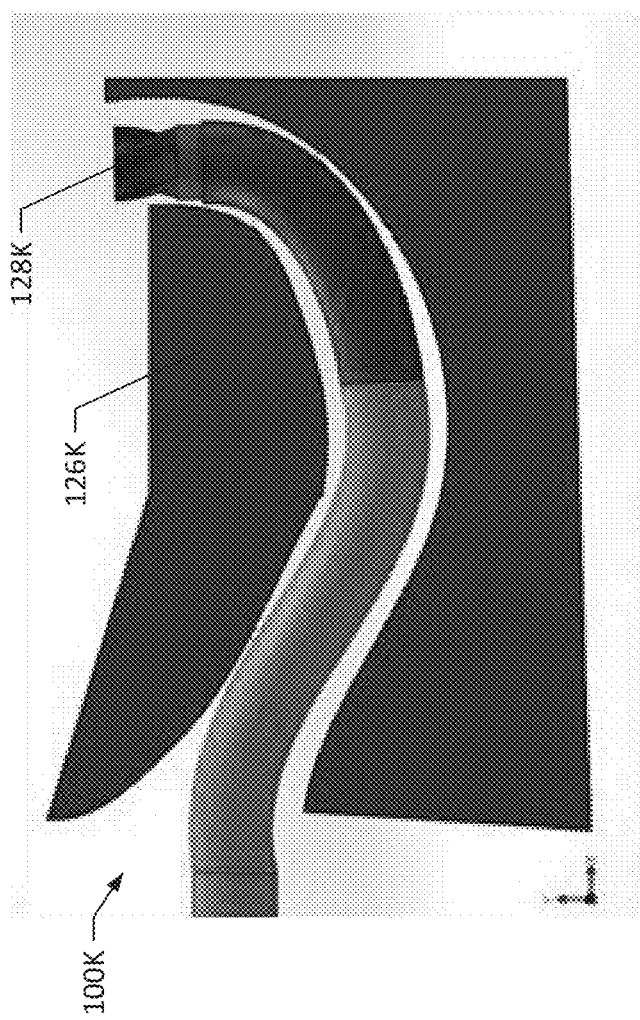
FIG. 12 illustrates navigation of a continuum device/manipulator employed as a steerable cutter around an obstacle according to an example embodiment.

FIG. 12 illustrates navigation of the continuum device/manipulator 100K employed as a steerable cutter to avoid an obstacle 126K according to an example embodiment. In an example embodiment, the continuum device/manipulator 100K may be snaked through a medium or around an obstacle 126K. As discussed above, the cutter 128 may extend from the distal end of the continuum device/manipulator 100K while being snaked or steered, or the cutter 128K may be passed through the lumen once the continuum device/manipulator 100K is in the desired position. By passing the cutter 128K through the lumen after positioning the continuum device/manipulator 100K, the cutting edge of the cutter 128K may not be exposed providing increased safety to the medium.

Figure 14:
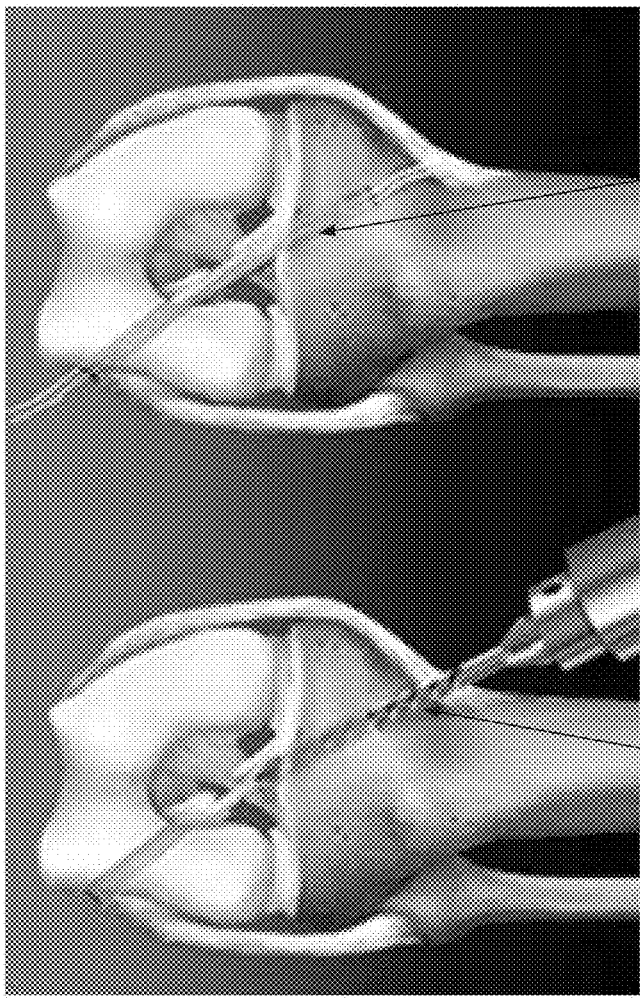
FIGS. 13 and 14 illustrate example medical applications of a continuum device/manipulator according to an example embodiment.
Figure 13:
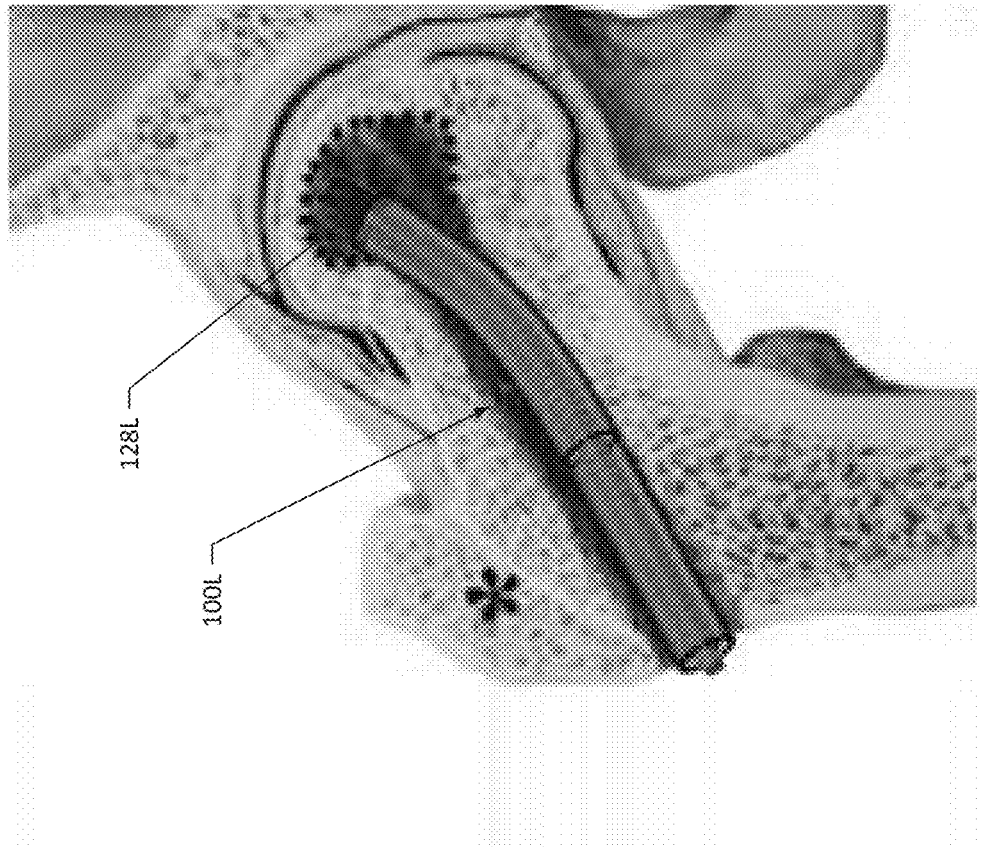

FIGS. 13 and 14 illustrate example medical applications of continuum device/manipulators according to an example embodiment. In the example depicted in FIG. 13, a continuum device/manipulator 100L is equipped with a cutting blade 128L. The continuum device/manipulator 100L may be used to drill a path to the ball of a hip joint. While drilling the relatively straight hole in the hip bone, the continuum device/manipulator 100L may be in the rigid state. Once the continuum device/manipulator 100L has reached the ball of the hip joint, the first segment of the continuum device/manipulator 100L may be transitioned to the soft state. In a first example, the first segment may be positioned and transitioned back to a rigid state to hollow out the ball of the hip joint. In a second example, the first segment may be maintained in the soft state, and the first segment may be steered in a sweeping motion to hollow the ball of the hip joint. In the instance in which the first segment is maintained in the soft state, the remaining segments may be maintained in the rigid state, such that only the first segment moves in the steering motion.

In the example depicted in FIG. 14, in order to support a traditional knee surgery, one or more holes may be drilled, by a hand drill 1400 for access. The drill holes may necessarily be straight, not allowing for in process correction and the drill is generally removed prior to proceeding to the operation to be performed. One or more traditional arthroscopic tools may be inserted into the one or more holes to perform the operation.

In contrast, in support of a knee surgery utilizing a continuum device/manipulator 100M, it may be possible for the continuum device/manipulator 100M to be steered, if necessary, during the drilling. Once the continuum device/manipulator 100M is in position the continuum device/manipulator 100M may be transitioned to the rigid state and cutter 128K removed and replaced with arthroscopic tools, such as grabber 124, without removing the continuum device/manipulator 100M. Additionally, the continuum device/manipulator 100M may be steered to additional positions, without necessarily drilling additional holes.

Figure 15:
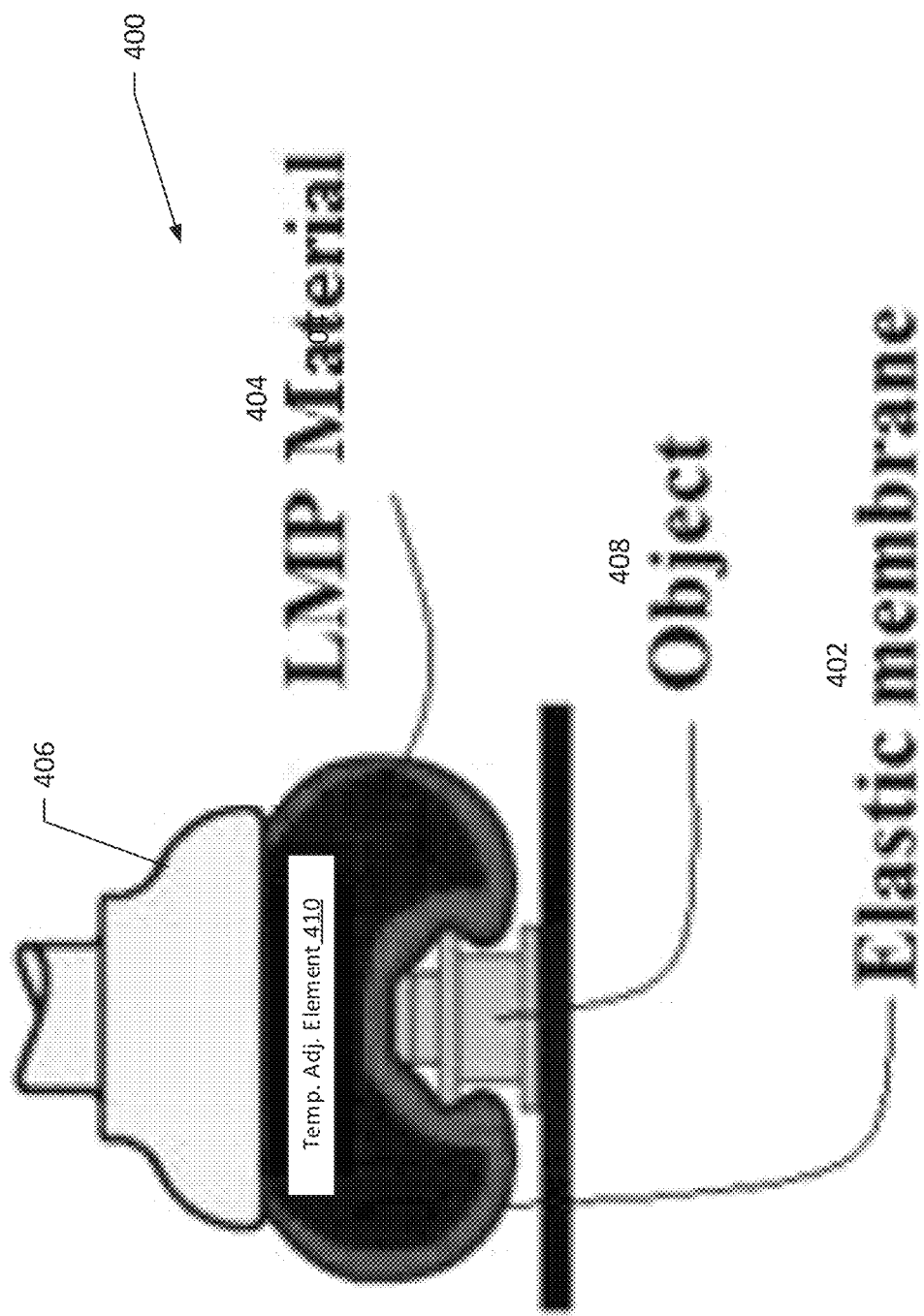
FIG. 15 illustrates a grasper according to an example embodiment.

FIG. 15 illustrates a grasper 400 according to an example embodiment. In an example embodiment, the grasper 400 may include an elastic or continuum membrane 402, such as silicon, latex, or the like. The membrane 402 may be filled with a LMP alloy 404, which may be substantially similar to the LMP alloy 104, as discussed above in reference to FIG. 3. The membrane 402 may be operably coupled to an end-effector of a positioning unit, such as a continuum device/manipulator 100, a robotic arm, a mobile robot, e.g. wheeled or track vehicle, or aerial vehicle.

A temperature adjustment element 410 may be disposed within the LMP alloy 404. The temperature adjustment element 410 may be substantially similar to the temperature adjustment element discussed above in FIG. 3. The temperature adjustment element 410 may be utilized to apply heat and/or cooling to change the phase of the LMP alloy 404, in substantially the same manner as discussed in FIG. 3.

In an example embodiment, the LMP alloy 404 may be in the liquid state allowing elasticity or flexibility of the membrane 402. The end effector 406 and or positioning unit may cause the membrane 402 to engage an object 408. The membrane 402 and LMP alloy 404 may conform to the contours of the object 408. The temperature adjustment element 410 may cause the LMP alloy 404 to transition to the solid phase, while the membrane 402 conforms to the contours of the object 408. The transition of the LMP alloy 404 to the solid phase may cause a rigid engagement of the object by the grasper 400.

Since the membrane 402 of grasper 400 can conform to the contours of the object, the grasper 400 may have significant grip strength while the LMP alloy 404 is in the solid phase, for example, a 20 g LMP alloy 404 grasper 400 may be capable or gripping greater than 2 kg. The solid phase, and therefore grip of the object, may be maintained indefinitely without applying power to the grasper 400. Additionally, since the grip of the grasper 400 is based on conformance to counters and not applying pressure to the object 408, the grasper 400 may be used to grasp sensitive materials, including without limitations mines and bombs.

FIGS. 16A-16C illustrate example positioning systems for the grasper 400 according to an example embodiment. FIG. 16A depicts a track robotic vehicle 500 including the grasper 400. FIG. 16B depicts a robotic arm 502 including the grasper 400. FIG. 16C depicts an aerial vehicle, e.g. drone, including the grasper 400.

Figure 17:
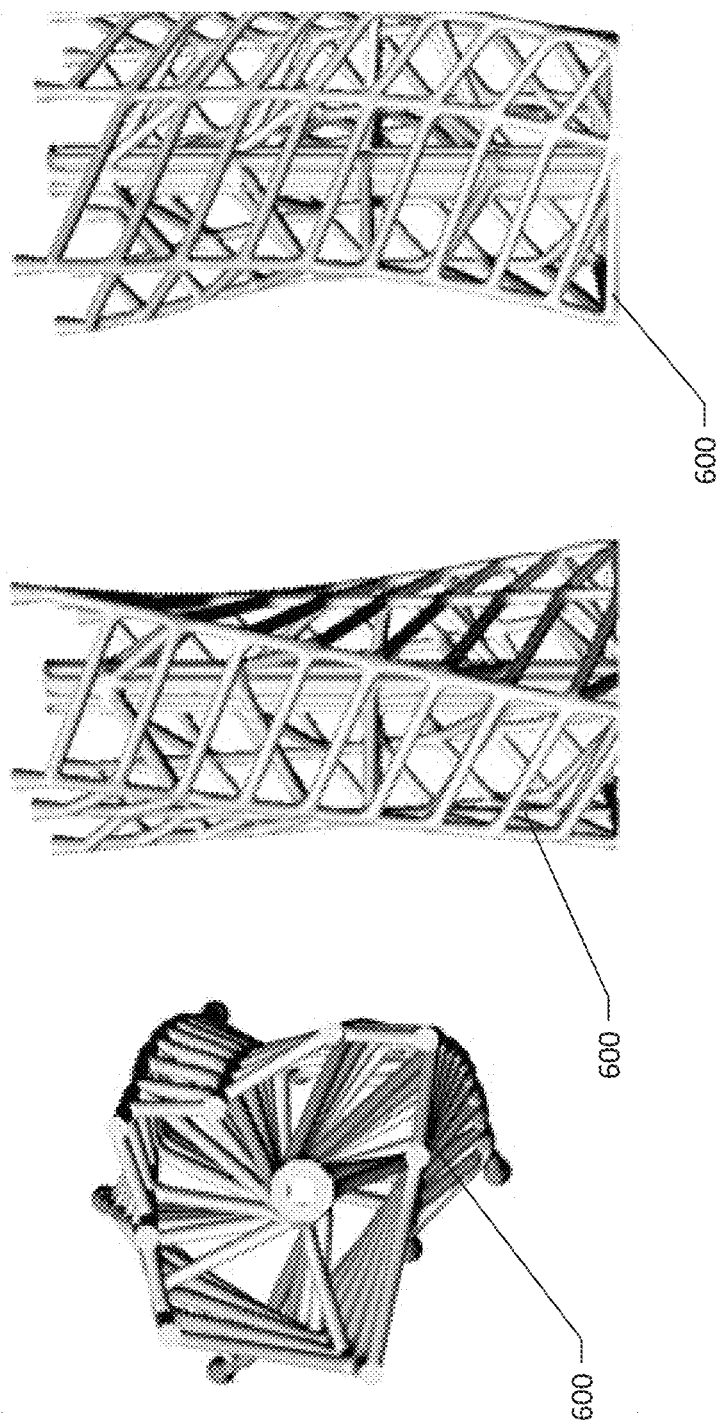
FIG. 17 illustrates a smart structure of a LMP alloy according to an example embodiment.

FIG. 17 illustrates a smart structure 600 according to an example embodiment. In an example embodiment, the LMP alloy 404 may be embedded into a smart structure 600. The smart structure 600 may be constructed by three dimensional printing and impregnated with the LMP alloy 404 in the liquid phase. The smart structure 600 may be silicon, latex, or other continuum or elastic material. The smart structure 600 may minimize the weight and cost of the grasper 400, while maintaining the maximum rigidity.

Example Controller

Figure 18:
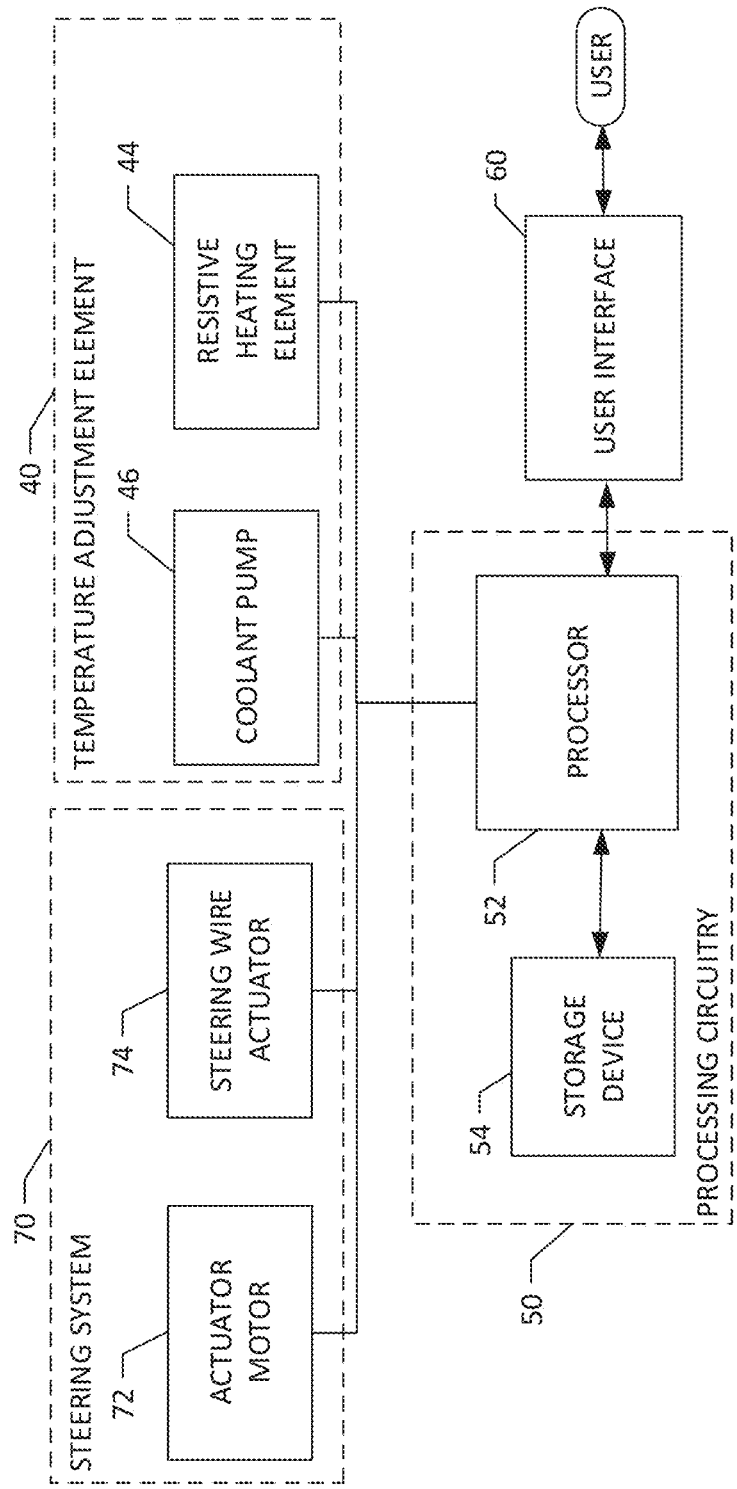
FIG. 18 illustrates an example controller for a continuum device/manipulator according to an example embodiment.

An example embodiment of the invention will now be described with reference to FIG. 18. FIG. 18 shows certain elements of a controller, e.g. electronic controller, for dynamically steering a continuum device/manipulator 100, controlling a positioning system, and/or applying heat or cooling to the LMP alloy 104, 404 according to an example embodiment. The controller of FIG. 18 may be employed, for example, on a client, a computer, a network access terminal, a personal digital assistant (PDA), cellular phone, smart phone, a network device, server, proxy, or the like. Alternatively, embodiments may be employed on a combination of devices. Accordingly, some embodiments of the present invention may be embodied wholly at a single device or by devices in a client/server relationship. Furthermore, it should be noted that the devices or elements described below may not be mandatory and thus some may be omitted in certain embodiments.

Referring now to FIG. 18, an apparatus configured for steering the continuum device/manipulator 100 or applying heat or cooling to the LMP alloy 104, 404 is provided. In an example embodiment, the controller may include or otherwise be in communication with processing circuitry 50 that is configured to perform data processing, application execution and other processing and management services. In one embodiment, the processing circuitry 50 may include a storage device 54 and a processor 52 that may be in communication with or otherwise control or be in communication with a temperature adjustment element 40 and/or a steering system 70. As such, the processing circuitry 50 may be embodied as a circuit chip (e.g., an integrated circuit chip) configured (e.g., with hardware, software or a combination of hardware and software) to perform operations described herein. However, in some embodiments, the processing circuitry 50 may be embodied as a portion of a server, computer, laptop, workstation or even one of various mobile computing devices. In situations where the processing circuitry 50 is embodied as a server or at a remotely located computing device, a user interface may be disposed at another device (e.g., at a computer terminal or client device) that may be in communication with the processing circuitry 50 via a device interface and/or a network).

In an example embodiment, the storage device 54 may include one or more non-transitory storage or memory devices such as, for example, volatile and/or non-volatile memory that may be either fixed or removable. The storage device 54 may be configured to store information, data, applications, instructions or the like for enabling the apparatus to carry out various functions in accordance with example embodiments of the present invention. For example, the storage device 54 could be configured to buffer input data for processing by the processor 52. Additionally or alternatively, the storage device 54 could be configured to store instructions for execution by the processor 52. As yet another alternative, the storage device 54 may include one of a plurality of databases that may store a variety of files, contents or data sets. Among the contents of the storage device 54, applications may be stored for execution by the processor 52 in order to carry out the functionality associated with each respective application.

The processor 52 may be embodied in a number of different ways. For example, the processor 52 may be embodied as various processing means such as a microprocessor or other processing element, a coprocessor, a controller or various other computing or processing devices including integrated circuits such as, for example, an ASIC (application specific integrated circuit), an FPGA (field programmable gate array), a hardware accelerator, or the like. In an example embodiment, the processor 52 may be configured to execute instructions stored in the storage device 54 or otherwise accessible to the processor 52. As such, whether configured by hardware or software methods, or by a combination thereof, the processor 52 may represent an entity (e.g., physically embodied in circuitry) capable of performing operations according to embodiments of the present invention while configured accordingly. Thus, for example, when the processor 52 is embodied as an ASIC, FPGA or the like, the processor 52 may be specifically configured hardware for conducting the operations described herein. Alternatively, as another example, when the processor 52 is embodied as an executor of software instructions, the instructions may specifically configure the processor 52 to perform the operations described herein.

In an example embodiment, the processor 52 (or the processing circuitry 50) may be embodied as, include or otherwise control the controller, which may be any means, such as, a device or circuitry operating in accordance with software or otherwise embodied in hardware or a combination of hardware and software (e.g., processor 52 operating under software control, the processor 52 embodied as an ASIC or FPGA specifically configured to perform the operations described herein, or a combination thereof) thereby configuring the device or circuitry to perform the corresponding functions of the temperature adjustment element 40 and/or steering system 70, as described below.

In some example embodiments, the temperature adjustment element 40 may be in wired or wireless communication with the processing circuitry 50. The temperature adjustment element 40 may include a coolant pump 46 and/or a resistive heating element 44. The processing circuitry 50 may cause the resistive heating element, such as spring 112D, to apply heat to the LMP alloy 104, 404 to cause the LMP alloy 104, 404 to transition to the liquid phase. For example, the processing circuitry 50 may control which wires 116D apply current to segments of the spring 112D, as discussed in reference to FIG. 3. The processing circuitry 50 may also terminate the application of heat to the LMP alloy 104, 404 causing a transition from the liquid phase to the solid phase.

In some example embodiments, the processing circuitry 50 may cause the coolant pump 46 to pump cold coolant through the cooling tube 113E and/or the lumen 108C. The cooling applied by the coolant may reduce the transition time of the LMP alloy 104, 404 from the liquid phase to the solid phase. Additionally or alternatively, the coolant pump may be configured to apply heat to the LMP alloy 104, 404 by pumping heated liquid through the cooling tube 113E and/or lumen 108C.

The processing circuitry 50 may be in wired or wireless communication with the steering system 70. The steering system 70 may include one or more actuator motors 72, such as actuator 122F, which may be configured to position joints, such as joints 120F. The steering system 70 may also include a steering wire actuator 74. The steering wire actuator 74 may be configured to apply force to one or more steering wires, such as steering wires 110C, to cause segments of the continuum device/manipulator 100, which are in the liquid phase to flex, bend, or be steered into a desired position.

In some example embodiments, the continuum device/manipulator may be further configured for additional operations or optional modifications. In this regard, in an example embodiment, the temperature adjustment element includes a resistive continuum heater. In some example embodiments, the temperature adjustment element includes a helical spring. In an example embodiment, the continuum device/manipulator also includes a power supply, a plurality of wires electrically connecting the temperature adjustment element to the power supply and a controller configured to control the temperature of the temperature adjustment element by energizing at least a portion of the temperature adjustment element. In some example embodiments, the temperature adjustment element includes a plurality of segments defined by the electrical connections of the plurality of wires and the controller is configured to control the temperature of at least two segments of the plurality of segments. In an example embodiment, the apparatus also includes a second continuum tube disposed within the first continuum tube. In some example embodiments, the LMP is disposed between the first continuum tube and the second continuum tube. In an example embodiment, the first continuum tube is helically disposed around the second continuum tube. In some example embodiments, the first continuum tube includes a lattice disposed around the second continuum tube. In an example embodiment, the temperature adjustment element includes a coolant pump configured to cause coolant to flow through the second continuum tube or a cooling tube. In some example embodiments, the continuum device/manipulator may also include a cutter configured to perform a cutting operation at a distal end of the second continuum tube. In an example embodiment, the cutter is configured to pass through the second continuum tube. In some example embodiments, the continuum device/manipulator also includes one or more non-continuum segments. In an example embodiment, the continuum device/manipulator also includes at least one motorized joint. In some example embodiments, the continuum device/manipulator also includes a manipulator disposed at a distal end of the first continuum tube. In an example embodiment, the manipulator includes a continuum membrane and the LMP is also disposed within the continuum membrane. The temperature adjustment element is further configured to apply heat or cooling to change the phase of the LMP within the continuum membrane and changing a phase of the LMP controls the flexibility of the continuum membrane.

In some example embodiments, the grasper may be further configured for additional operations or optional modifications. In this regard, in an example embodiment, the manipulator is configured to cause the continuum membrane to engage an object in an instance in which the LMP is in a liquid phase and then cause the temperature adjustment element to cause the LMP to change to a solid phase. Change to the solid phase causes a rigid engagement of the continuum membrane and the object. In an example embodiment, the manipulator also includes a positioning system configured to move the continuum membrane to a desired position. In some example embodiments, the positioning system is a robotic arm, a wheeled vehicle, an aerial vehicle, or a continuum device/manipulator.

Many modifications and other embodiments of the devices set forth herein will come to mind to one skilled in the art to which these inventions pertain having the benefit of the teachings presented in the foregoing descriptions and the associated drawings. Therefore, it is to be understood that the measuring devices are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:
1. A continuum device/manipulator comprising:
a first flexible tube;
a second flexible tube disposed within an inner opening of the first flexible tube;
a low melting point (LMP) alloy disposed between the first flexible tube and the second flexible tube; and
a temperature adjustment element comprising a helical spring, the temperature adjustment element being configured to apply heating to temperatures above a melting point of the LMP alloy or cooling to temperatures below the melting point of the LMP alloy to change a phase of the LMP alloy, wherein changing the phase of the LMP alloy controls a flexibility of the continuum device/manipulator by changing the LMP alloy between a liquid state and a solid state, the helical spring being coiled around the second flexible tube;
a plurality of wires comprising at least three wires and electrically connected to the helical spring to form electrically controllable segments between electrical connections of the plurality of wires to the helical spring, each wire of the plurality of wires being electrically connected to the helical spring at a different location on the helical spring; and
a controller configured to control a temperature of the temperature adjustment element at each segment by selectively energizing the wires of the plurality of wires;
wherein the helical spring, the plurality of wires, and the electrical connections between the plurality of wires are disposed between the first flexible tube and the second flexible tube and are embedded within and surrounded by the LMP alloy.
2. The continuum device/manipulator of claim 1, wherein the helical spring is configured to operate as a resistive flexible heater by passing an electric current through the helical spring, and wherein the LMP alloy is disposed in a space formed by an inner surface of the first flexible tube and an outer surface of the second flexible tube.

3. The continuum device/manipulator of claim 1, further comprising a power supply electrically connected to the plurality of wires.

4. The continuum device/manipulator of claim 1, wherein the temperature adjustment element comprises a coolant pump configured to cause coolant to flow through the second flexible tube or through a cooling tube.

5. The continuum device/manipulator of claim 1, further comprising: one or more non-continuum segments.

6. The continuum device/manipulator of claim 1, further comprising a motorized joint comprising a motor disposed at a joint of the continuum device/manipulator.

7. The continuum device/manipulator of claim 1, further comprising: a grasper disposed at a distal end of the first flexible tube.

8. The continuum device/manipulator of claim 1, wherein the second flexible tube comprises an opening that forms a lumen of the continuum device/manipulator, the lumen being configured to provide passage for items from a proximal end to a distal end of the continuum device/manipulator.

9. The continuum device/manipulator of claim 1, further comprising a cooling tube disposed within the LMP alloy.

10. The continuum device/manipulator of claim 1, wherein the LMP alloy has a melting point at sixty-two degrees Celsius.

11. The continuum device/manipulator of claim 1, wherein the LMP alloy comprises bismuth, indium, and tin.

12. The continuum device/manipulator of claim 1, further comprising steering wires anchored between a collar and an end of the continuum device/manipulator and configured to actuate to bend the continuum device/manipulator when positioning at least one segment adjacent to the LMP alloy that is not in a solid state, the steering wires being formed of a shape memory alloy.

13. The continuum device/manipulator of claim 12, wherein the shape memory alloy is Nitinol.

14. The continuum device/manipulator of claim 1, wherein the first flexible tube is helically disposed around the second flexible tube.

15. The continuum device/manipulator of claim 1, wherein the first flexible tube comprises a lattice disposed around the second flexible tube.

16. The continuum device/manipulator of claim 1, further comprising a cutter configured to perform a cutting operation at a distal end of the second flexible tube.

17. The continuum device/manipulator of claim 16, wherein the cutter is configured to pass through the second flexible tube.

18. An apparatus comprising:
a first flexible tube;
a second flexible tube disposed within an inner opening of the first flexible tube;
a low melting point (LMP) alloy disposed between the first flexible tube and the second flexible tube; and
a temperature adjustment element configured to apply heating to temperatures above a melting point of the LMP alloy or cooling to temperatures below the melting point of the LMP alloy to change a phase of the LMP alloy, wherein changing the phase of the LMP alloy controls a flexibility of the continuum device/manipulator by changing the LMP alloy between a liquid state and a solid state;
wherein the temperature adjustment element comprises a cooling tube coiled around the second flexible tube and configured to pass coolant or hot fluid through the cooling tube;
wherein the temperature adjustment element comprises a helical spring coiled around the second flexible tube;
wherein the apparatus further comprises a plurality of wires comprising at least three wires electrically connected to the helical spring to form electrically controllable segments of the helical spring, each wire of the plurality of wires being electrically connected to the helical spring at a different location on the helical spring; and
a controller configured to control a temperature of the temperature adjustment element at each segment by selectively energizing the wires of the plurality of wires;
wherein the helical spring, the plurality of wires, the electrical connections between the plurality of wires, and the cooling tube are disposed between the first flexible tube and the second flexible tube and are embedded within and surrounded by the LMP alloy.

* * * * *